US012566230B2

(12) United States Patent
Kulam Najmudeen et al.

(10) Patent No.: US 12,566,230 B2
(45) Date of Patent: Mar. 3, 2026

(54) TAMPERLESS TENSOR ELASTOGRAPHY IMAGING

(71) Applicant: The United States of America, as represented by the Secretary, Department of Health and Human Services, Bethesda, MD (US)

(72) Inventors: Magdoom Mohamed Kulam Najmudeen, Silver Spring, MD (US); Peter J. Basser, Washington, DC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 120 days.

(21) Appl. No.: 18/563,237

(22) PCT Filed: May 25, 2022

(86) PCT No.: PCT/US2022/030846
§ 371 (c)(1),
(2) Date: Nov. 21, 2023

(87) PCT Pub. No.: WO2022/251308
PCT Pub. Date: Dec. 1, 2022

(65) Prior Publication Data
US 2024/0377491 A1 Nov. 14, 2024

Related U.S. Application Data

(60) Provisional application No. 63/192,920, filed on May 25, 2021.

(51) Int. Cl.
*A61B 5/055* (2006.01)
*A61B 8/00* (2006.01)
(Continued)

(52) U.S. Cl.
CPC .......... *G01R 33/5608* (2013.01); *A61B 5/055* (2013.01); *A61B 8/485* (2013.01);
(Continued)

(58) Field of Classification Search
CPC ......... G01S 33/56357; G01S 33/56358; A61B 5/055
See application file for complete search history.

(56) References Cited

U.S. PATENT DOCUMENTS

| | | | |
|---|---|---|---|
| 5,592,085 A | 1/1997 | Ehman | |
| 8,643,369 B2 * | 2/2014 | Krzyzak | .......... G01R 33/56341 324/309 |

(Continued)

FOREIGN PATENT DOCUMENTS

| WO | WO 2018/031942 A1 | 2/2018 |
|---|---|---|

OTHER PUBLICATIONS

Fukuzaki et al., "The ability of line scan diffusion imaging method comparison with echo planner diffusion imaging," *International Society for Magnetic Resonance in Medicine*, abstract, p. 1833 (1999).
(Continued)

*Primary Examiner* — Colin T. Sakamoto
(74) *Attorney, Agent, or Firm* — Leydig, Voit & Mayer, Ltd.

(57) ABSTRACT

Magnetic resonance and ultrasound methods can produce estimates of full rank-4 elasticity tensors (E-tensors) using suitable constraints. E-tensor estimates can be based on E-tensor symmetry conditions and a suitable E-tensor selected from among a set of E-tensors calculated using different symmetry constraints. Displacement fields used in E-tensor calculations can be noise reduced using compatibility conditions. With the selected E-tensor, various stains that are rotation invariant can be computed. In one example,
(Continued)

SELECT SPECIMEN VOLUME OF INTEREST
402

ACQUIRE DISPLACEMENT DATA AT SELECTED FREQUENCY f; *u(x)*
404

DENOISE *u(x)*
406

ESTIMATE E-TENSOR BASED ON DENOISED *u(x)* AND MODEL SUBJECT TO POSITIVE DEFINITENESS CONSTRAINT
408

SELECT E-TENSOR MODEL
406

MORE E-TENSOR MODELS?
410

SELECT E-TENSOR- BASED ON COMPARISONS OF MODEL ESTIMATE
412

SELECT STAIN(S)
414

OUTPUT E-TENSOR, K, G, MA, AS, AND/OR QUARTIC GLYPH
416

400 an E-tensor for an in vivo brain is computed using the mechanical disturbance associated with cardiac pulsations. The selected E-tensor and associated stains, physiological disorders such as Alzheimer's disease and traumatic brain injury (TBI) and even neural activation may be more readily detected than with conventional methods that do not use the full E-tensor.

20 Claims, 8 Drawing Sheets

(51) Int. Cl.

| | |
|---|---|
| *G01R 33/54* | (2006.01) |
| *G01R 33/56* | (2006.01) |
| *G01R 33/563* | (2006.01) |

(52) U.S. Cl.
CPC .......... *A61B 8/5207* (2013.01); *G01R 33/543* (2013.01); *G01R 33/56358* (2013.01)

(56) References Cited

U.S. PATENT DOCUMENTS

| | | | | |
|---|---|---|---|---|
| 9,965,852 | B2 | 5/2018 | Romano | |
| 10,295,645 | B2 * | 5/2019 | Tsai ...................... | G01R 35/005 |
| 10,545,211 | B2 * | 1/2020 | Harris .............. | G01R 33/56572 |
| 2003/0222647 | A1 * | 12/2003 | Goldie ................. | G01R 33/385 324/318 |
| 2009/0284257 | A1 * | 11/2009 | Bammer .......... | G01R 33/56509 324/307 |
| 2010/0271021 | A1 * | 10/2010 | Liu .................. | G01R 33/56341 324/309 |
| 2014/0316245 | A1 * | 10/2014 | Romano ................ | A61B 5/055 600/410 |
| 2016/0069974 | A1 * | 3/2016 | Lee .................... | G01R 33/5611 324/309 |
| 2020/0323479 | A1 * | 10/2020 | Romano ............ | G01R 33/5608 |
| 2023/0342885 | A1 * | 10/2023 | Zhao ......................... | G06T 5/70 |
| 2023/0349994 | A1 * | 11/2023 | Sacolick .............. | G01R 33/543 |

OTHER PUBLICATIONS

Pierpaoli et al., "Polyvinylpyrrolidone (PVP) water solutions as isotropic phantoms for diffusion MRI studies," *Proc Intl Mag Reson Med*, 17:1414 (2009).

Burnham et al., "Model selection and inference: a practical information-theoretic approach," pp. 70-71, Springer (1998).

Chaze et al., "Physiomechanical noise in brain magnetic resonance elastography," *Proceeding of the International Society for Magnetic resonance in Medicine, 26th Annual Meeting and Exhibition*, Paris, France, vol. 26 (5596), Jun. 16-21, 2018.

Chi-Wang, "Essentially non-oscillatory and weighted essentially non-oscillatory schemes," *Acta Numerica*, 29, 701-762 (2020).

Correia et al., "3D elastic tensor imaging in weakly transversely isotropic soft tissues," *Phys. Med. Biol.*, 63 (15), 1-14 (2018).

Cowin, "Properties of the Anisotropic Elasticity Tensor," *Mech. Appl. Math.*, vol. 42, pt. 2, 249-266 (May 1989).

European Patent Office, International Search Report, Application No. PCT/US2022/030846, mailed Sep. 13, 2022, 8 pages.

European Patent Office, Written Opinion of the International Searching Authority, Application No. PCT/US2022/030846, mailed Sep. 13, 2022, 14 pages.

Georgiyevskii et al., "The number of independent compatibility equations in the mechanics of deformable solids," *J. Applied Mathematics and Mechanics*, 68 (6), 941-946 (2004).

Guchhait et al., "Anisotropic linear elastic parameter estimation using error in the constitutive equation functional," *Royal Society of London. Proc. R. Soc. A.*, 472 (2192), 1-20 (2016).

Helbig, "Foundations of anisotropy for exploration seismics," Handbook of Geophysical Exploration, Section I, Seismic Explorations, vol. 22: 405-408 (1994).

Lanczos, C., "Applied Analysis," Dover Publications pp. 321-324 (1988).

Norris, "Elastic moduli approximation of higher symmetry for the acoustical properties of an anisotropic material," *J. Acoust. Soc. Am.*, 119 (4), 2114-2121 (2006).

Nye, J., "Physical Properties of Crystals," Oxford, pp. 140-141 (1957).

Qin et al., "Combining MR elastography and diffusion tensor imaging for the assessment of anisotropic mechanical properties: A phantom study," *J. Magn. Reson. Imaging*, 37 (1), 217-226 (2012).

Sinkus et al., "Imaging anisotropic and viscous properties of breast tissue by magnetic resonance-elastography," *Magn. Reson. Med.*, 53 (2), 372-387 (2005).

Weaver et al., "Brain Mechanical Property Measurement Using MRE with Intrinsic Activation," *Phys. Med. Biol.*, 57 (22), 7275-7287 (2012) Author Manuscript.

* cited by examiner

304 — PROCESSOR/ CONTROLLER

DELAY — 306

302

CARDIAC CYCLE DETECTOR

RF COILS FOR APPLYING DISPLACEMENT - ENCODING PULSE SEQUENCES

DETECTOR COILS

310

308

300

RECEIVE DENOISED $u(x_j)$ AND
SELECTED MODEL
452

SOLVE OPTIMIZATION PROBLEM SUBJECT TO
POSITIVE DEFINITENESS CONSTRAINT TO
OBTAIN VALUES of $c_i$ FOR $i$ =1, 2, 3
454

OBTAIN $C_{ijsm}$ BASED on $c_i$
456

450

TAMPERLESS TENSOR ELASTOGRAPHY IMAGING

CROSS-REFERENCE TO RELATED APPLICATIONS

This patent application is the U.S. national phase of International Application No. PCT/US2022/030846, filed on May 25, 2022, which claims the benefit of U.S. Provisional Patent Application No. 63/192,920, filed May 25, 2021, the disclosures of which are incorporated by reference herein in their entireties for all purposes.

STATEMENT REGARDING FEDERALLY SPONSORED RESEARCH OR DEVELOPMENT

This invention was made with Government support under project number HD00897203 by the National Institutes of Health, National Institute of Child Health and Human Development. The United States Government has certain rights in the invention.

FIELD OF THE DISCLOSURE

The disclosure pertains to estimation of the elasticity tensor using magnetic resonance (MR), ultrasound, and other displacement encoding techniques.

BACKGROUND OF THE INVENTION

Changes in material properties such as stiffness represent a sensitive measure of underlying changes in tissue architecture, organization, and microstructure. In terms of non-invasive imaging parameters used to assess tissue changes, quantities like $T_1$, $T_2$, $T_2$*Magnetic Resonance Imaging (MRI) relaxation times or diffusivity may change only by a few percent in diseases such as in Alzheimer's and traumatic brain injury (TBI), whereas mechanical properties such as tissue stiffness may change by orders of magnitude.

Elastography techniques used to map the material stiffness typically involve measuring the displacement resulting from shear waves of known frequency imposed on the material by an external actuator, vibrator, or tamper. The material stiffness is then estimated from the measured displacement field by inverting a model relating the material's strain to the material's stress. Two popular elastography imaging technologies used in clinics are MR elastography (MRE) and ultrasound elastography (USE). Despite their success in characterizing isotropic tissues, such as the liver, the applications to anisotropic tissues such as the brain, heart, muscle, kidney, cartilage, etc., have been very limited. In anisotropic materials, the shear wave velocity is dependent on the direction of the applied shear wave, which introduces variability in the elastograms generated from the conventional techniques depending on the orientation of the tamper or direction of the shear wave propagation front relative to the material axes.

An adequate description of a constitutive law relating the stress and strain in an anisotropic material requires a rank-4 anisotropic elasticity tensor (E-tensor) with a number of free parameters ranging from 2 to 21 depending on the degree of material symmetry instead of the 1-parameter isotropic scalar shear modulus used in conventional methods. Reconstructing the full E-tensor from a single mechanical excitation is an ill-posed inverse problem since the number of unknowns typically exceeds the number of available equations. A class of anisotropic MRE studies partly overcomes this ill-posedness by assuming that the rank-2 diffusion tensor obtained from diffusion tensor imaging (DTI), and the rank-4 E-tensor share the same fiber reference frame. This assumption is not generally true due to the known limitations of the DTI model in accounting for complex tissue geometries such as crossing/splaying/kissing fibers in the brain. This approach also limits the symmetry of the reconstructed E-tensor to be no more complex than the 9-parameter orthotropic material model.

For an accurate estimation of stiffness using elastography techniques, it is essential to cause a sufficiently large deformation of the material. The high frequency of operation of most tampers used to reduce the MR echo time with oscillating displacement encoding gradients in MRE, and the ease of using the same probe for generating and detecting shear waves in ultrasound (i.e., acoustic radiation force impulse, ARFI imaging) poses several challenges. It impedes the transmission of mechanical energy into organs surrounded by bony structures such as the heart and brain as the applied energy is largely reflected due to impedance mismatch at the bone-tissue interface. The energy transmitted into the tissue is further dampened due to dissipation within the tissue which typically increases with increasing frequency. Thus, large tamper amplitudes may be required to generate sufficient deformation of the tissue which could potentially preclude certain patient cohorts, such as those diagnosed with TBI for brain imaging. In addition, the higher rate of reflections of the incident shear wave within the tissue that comes with increasing frequency requires solving a complex boundary value problem, for instance by using the finite element method (FEM) or other numerical techniques, which account for these effects as opposed to direct voxelwise estimation of the E-tensor.

A more pragmatic and insightful approach is to use the intrinsic deformation of the tissue caused by physiological motion such as from cardiac pulsation and/or respiratory motion, which has not been used to characterize mechanical anisotropy. The very low frequency of physiological excitation results in less wave attenuation and fewer reflections from internal boundaries. In organs such as the brain, this deformation is amplified naturally due to the presence of the skull (i.e., Monroe-Kellie doctrine). There are several MRI and ultrasound imaging methods to measure the physiological deformation of organs such as displacement encoding with stimulated echoes (DENSE), harmonic phase (HARP) imaging for MRI, and speckle tracking and Doppler based methods for ultrasound with differing advantages and drawbacks. DENSE imaging, while highly sensitive to small displacements, suffers from 50% signal loss compared to spin echo MR and introduces well-known artifacts arising from the use of multiple radio frequency (RF) pulses. Ultrasound, while portable and relatively inexpensive, is not typically well suited for brain imaging due to the high acoustic attenuation of the skull. New approaches are needed to efficiently measure the physiological deformation of tissues and reconstruct the full rank 4 E-tensor to permit satisfactory characterization and remote palpation of brain tissue as well as other biological and non-biological materials.

BRIEF SUMMARY OF THE INVENTION

The disclosure pertains to elastography techniques that permit measurement of small physiological tissue displacements using spin echo MRI, ultrasound, or other techniques, reconstruction of a full rank-4 anisotropic elasticity tensor (E-tensor) along with strategies that denoise the measured displacement field using physically motivated compatibility conditions, and a family of new intrinsic, invariant stains or parameters to characterize different features of the measured E-tensor. The disclosed E-tensor estimation pipelines can be evaluated using simulated 3D displacement data in the presence of noise, and displacement measurements in an anisotropic material embedded in an agarose phantom can confirm the applicability of the disclosed approaches.

In some examples, the disclosed elastography methods and apparatus are applied to brain tissue using the intrinsic tissue deformation caused by cardiac pulsation as a means of mechanically actuating the tissue endogenously as opposed to the use of an exogenous actuator. The data is efficiently acquired along all segments of the cardiac cycle and can be sensitive to slow deformations of the brain parenchyma with heart beat. Cardiac pulsation can be similarly used with other tissues in vivo. However, biological or non-biological specimens can be measured without using cardiac pulsation using, for example, a tamper or actuator or other physiological movement, such as respiration.

Methods are disclosed that include obtaining a displacement field within a specimen and, based on the displacement field and one or more constraints, estimating at least two elements of an elasticity tensor associated with the specimen. In examples, the displacement field within the specimen is associated with a selected frequency. In a representative example, the displacement field is obtained based on a plurality of multidirectional displacement-sensitized MR signals associated with the specimen at the selected frequency. The multidirectional displacement-sensitized MR signals can be associated with a plurality of specimen voxels, the specimen displacements are determined for each of the plurality of voxels, and the at least two elements of the elasticity tensor associated with the specimen are determined for each of the plurality of voxels. In examples, the estimate of the at least two elements of the elasticity tensor is determined with the at least two elements constrained to be positive definite. The estimate of the at least two elements of the elasticity tensor can be determined based on symmetry group compatibility. In some examples, the at least two elements of the elasticity tensor includes all elements of the elasticity tensor. In representative example, the determined specimen displacements are denoised and the at least two elements of the elasticity tensor are estimated based on the denoised displacements using, for example, compatibility conditions. In an example, the multidirectional displacement-sensitized magnetic resonance signals synchronized with the mechanical excitation of the specimen are obtained by applying a plurality of gradient pulse pairs with a temporal separation of at least 20 ms and a 180 degree RF pulse between each of the gradient pulse pairs. In some examples, the estimates of the at least two elements are processed to produce an orientation invariant indicator of specimen elasticity, wherein the orientation invariant indicator of specimen elasticity is one or more of a bulk average stiffness, a mechanical anisotropy, a bulk shear modulus, or an effective anisotropy. In some examples, the at least two elements of the elasticity tensor are processed to produce a visual indicator of specimen elasticity, wherein the visual indicator is a glyph. In some examples, the specimen excitation is produced in vivo by one or more heartbeats and the specimen is an in vivo brain. In other examples, a mechanical disturbance is applied at the selected frequency with an actuator, wherein the plurality of multidirectional displacement-sensitized MR signals associated with a specimen are responsive to the applied mechanical disturbance. In other examples, the displacement field is obtained based on a plurality of multidirectional displacement-sensitized acoustic signals associated with the specimen at the selected frequency.

A MR apparatus is provided that includes a magnet operable to establish an axial magnetic field, at least one gradient coil situated to apply displacement-sensitizing gradient pulses to a specimen situated in the axial magnetic field, at least one receiver coil situated to receive MR signals responsive to the displacement-sensitizing gradient pulses, and a processor situated to receive the MR signals and produce an estimate of at least two components of an elasticity tensor associated with at least one voxel of the specimen. In some examples, the processor is configured to produce an estimate of all components of the elasticity tensor for a plurality of voxels and/or to produce at least one orientation invariant index of elasticity based on the components of the elasticity tensor for a plurality of voxels. In some examples, the gradient coils are operable to produce gradient pulse pairs about a 180 degree RF pulse and having a temporal separation of at least 20 ms. In additional examples, the processor is configured to determine a displacement field, denoise the displacement field, and produce a full elasticity tensor based on the denoised displacement field. In some examples, the denoising is based on compatibility conditions and/or the processor is configured to determine a full elasticity tensor based on a positive definiteness constraint and/or to determine a full elasticity tensor based on a comparison of elasticity tensors calculated based on two or more symmetry conditions. In some examples, the gradient coils are operable to apply the displacement-sensitizing gradients at a plurality of times in an acoustic excitation period of the specimen.

Methods are disclosed that include obtaining a measured displacement field associated with a specimen, wherein the measured displacement field is responsive to a mechanical disturbance at a fixed frequency, reducing noise in the measured displacement field based on applying compatibility conditions, for a plurality of elasticity tensor symmetries, obtaining corresponding elasticity tensor estimates, wherein each of the estimates is based on a selected symmetry and a positive definiteness constraint, and selecting one of the elasticity tensor estimates from the plurality to represent the specimen based on goodness-of-fit and a number of fit parameters. In typical examples, a rotationally invariant indicator of elasticity is determined based on the selected elasticity tensor estimate.

Methods are disclosed for measuring an elasticity tensor of a brain in vivo, the methods include measuring a cardiac-induced displacement field in the brain, based on the cardiac-induced displacement field and a positive-definiteness constraint on the elasticity tensor, calculating two or more potential elasticity tensors, and selecting one of the potential elasticity tensors as representative of the brain.

The foregoing and other features will become more apparent from the following detailed description of several embodiments, which proceeds with reference to the accompanying figures.

BRIEF DESCRIPTION OF THE DRAWING(S)

DETAILED DESCRIPTION OF THE INVENTION

Introduction

Figure 1:
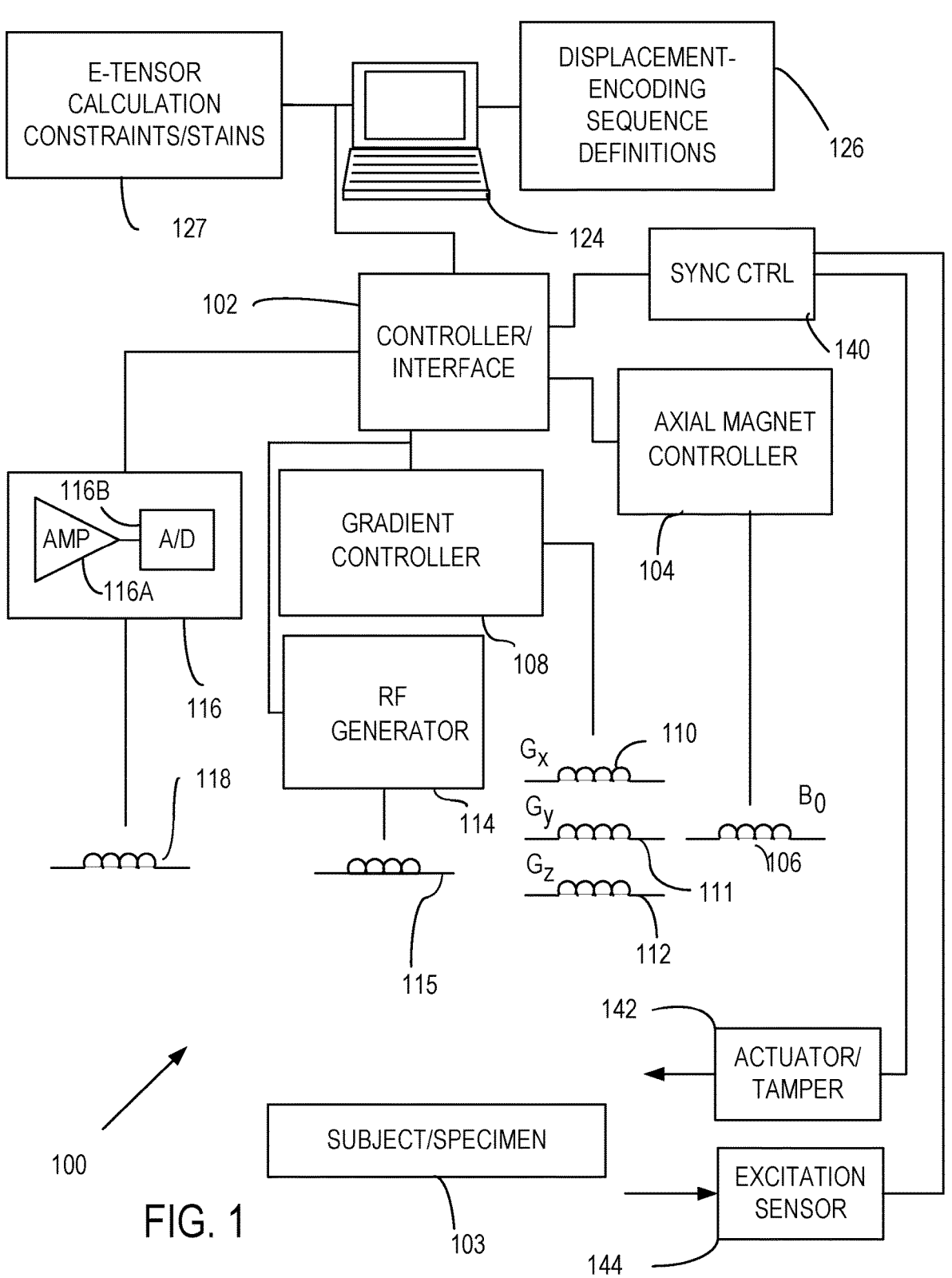
FIG. 1 illustrates a representative MR system operable to apply displacement encoding pulse sequences and provide measurements of a displacement field at one or more locations in a specimen based on the displacement encoding.

For purposes of description, particular arrangements of three-dimensional spatial coordinates are used such as (x, y, z) or $(x_1, x_2, x_3)$, and a static or axial magnetic field for MR measurement is applied along a z-axis (or an $x_3$-axis) and is referred to as $B_0$.

The disclosure pertains generally to estimation of anisotropic mechanical properties of biological and other materials and, in particular, a full E-tensor. Tissue stiffness changes in a variety of normal and pathological conditions including during development, neuronal activity, cancer, Alzheimer's disease, and traumatic brain injury (TBI). The degree of these changes is also far greater compared to traditional imaging contrast mechanisms such as $T_1$-weighted and diffusion or diffusion-weighted MRI, which makes stiffness changes a potentially more sensitive probe for brain structure and function assessment. For example, the static shear modulus of two gray matter regions in the brain (cerebral cortex and putamen) can differ by almost 250% while their isotropic mean diffusivities are indistinguishable and $T_1$ relaxation times differ only by 10%. Other specimens can be similarly characterized as well.

According to some disclosed approaches, full E-tensor measurements can be made non-invasively. As discussed above, conventional approaches generally impose a shear wave of known frequency in a material with an external actuator and use an isotropic inversion model. The resulting displacement can be measured using a plethora of displacement encoding methods synchronized to the external stimulus and tissue elasticity can be reconstructed from the measured displacement using an isotropic inversion model. While such approaches are suitable for characterizing isotropic tissues, these approaches are not suitable for characterizing anisotropic tissues such as the brain, heart, skeletal muscle, intervertebral disc, kidney, and/or cartilage. An adequate representation of anisotropic tissue requires a rank-4 anisotropic elasticity tensor (E-tensor) with the number of free parameters ranging from 2 to 21 depending on the material symmetry, not the isotropic scalar shear modulus used in conventional approaches.

Unlike conventional approaches, the disclosed methods and apparatus can fully characterize the rank-4 E-tensor in tissues. The disclosed approaches can be referred to as tensor elastography and can reconstruct a complete rank-4 E-tensor of tissues (or other specimens) without imposing any particular symmetry requirements on the tensor. The reconstruction pipeline is theoretically evaluated below using simulations in the presence and absence of noise, and could be experimentally verified using an agar phantom embedded with an anisotropic material. In addition, a spin echo MRI method to measure small tissue displacements is disclosed along with novel denoising strategies for the measured displacement field by locally enforcing compatibility conditions. A way to apply the invention using ultrasound imaging is also disclosed. As used herein, a displacement field generally refers to specimen displacement $u_i$ in three dimensions and as a function of location $(x_1, x_2, x_3)$ in the specimen, wherein $u_i$ are components of the displacement field along an $x_i$-axis. A family of invariant stains is introduced to characterize and visualize different aspects of the E-tensor to simplify evaluation of the E-tensor and to enable such quantities to be measured and mapped.

Representative MR Measurement Apparatus

MR measurements as disclosed can be obtained and processed using an MRI apparatus 100 as illustrated in FIG. 1. The apparatus 100 includes a controller/interface 102 that can be configured to apply selected magnetic fields such as constant or pulsed field gradients to a subject 103 or other specimen. An axial magnet controller 104 is in communication with an axial magnet 106 that is generally configured to produce a substantially constant magnetic field $B_0$. A gradient controller 108 is configured to apply constant or time-varying magnetic field gradients in one or more selected directions or in a set of directions using magnet coils 110-112 to produce respective magnetic field gradient vector components $G_x$, $G_y$, $G_z$ or combinations thereof to produce displacement encodings. An RF generator 114 is configured to deliver one or more RF pulses such as 90 degree or 180 degree pulses to a specimen using an RF transmitter coil 115. An RF receiver 116 is in communication with an RF receiver coil 118 and is configured to detect or measure net magnetization of spins. Typically, the RF receiver includes an amplifier 116A and an analog-to-digital converter 116B that detect and digitize received signals to obtain MR signals responsive to the displacement encoding. Slice selection gradients can be applied with the same hardware used to apply the diffusion gradients. The gradient controller 108 can be configured to produce pulses or other gradient fields along one or more axes as needed.

For imaging, specimens are divided into volume elements (voxels) and MR signals for a plurality of gradient directions are acquired, but signals can be acquired for one or only a few specimen voxels as well. In typical examples, signals are obtained for some or all voxels of interest. A computer 124 or other processing system such as a personal computer, a workstation, a personal digital assistant, laptop computer, smart phone, or a networked computer can be provided for acquisition, control, and/or analysis of specimen data. The computer 124 generally includes a hard disk, a removable storage medium such as a thumb drive, and other memory such as random access memory (RAM). Data can also be transmitted to and from a network using Cloud-based processors and storage. Data could be uploaded to the Cloud or stored elsewhere. Computer-executable instructions for data acquisition or control, displacement-encoding pulse sequence selection, acquisition and denoising of displacement data, determination of material parameter values, or conformance to one or more constraints associated with E-tensor symmetry can be provided on one or more storage media such as memories 126, 127, or delivered to the computer 124 via a local area network, the Internet, or other network. Signal acquisition, instrument control, and signal analysis can be performed with distributed processing. For example, signal acquisition and signal analysis can be performed at different locations. Signal evaluation can be performed remotely from signal acquisition by communicating stored data to a remote processor. In general, control and data acquisition with an MRI apparatus can be provided with a local processor, or via remote instructions and data transmitted using a network.

The apparatus 100 also includes a sync controller 140 that can be coupled to an actuator (or tamper) 142 that can be used to generate a mechanical disturbance in the specimen 103. An excitation sensor 144 can also be included such as a sensor that is responsive to a cardiac cycle or other disturbance. In the examples below, external excitations are not generally applied as cardiac pulsation is used, but the disclosed methods and apparatus can be used with or without external actuators or tampers and the use of the cardiac cycle is a convenient example. Using the apparatus 100, a displacement field $u_i$ can be measured.

Displacement Encoding MRI Pulse Sequences for E-Tensor Measurement

Figure 2:
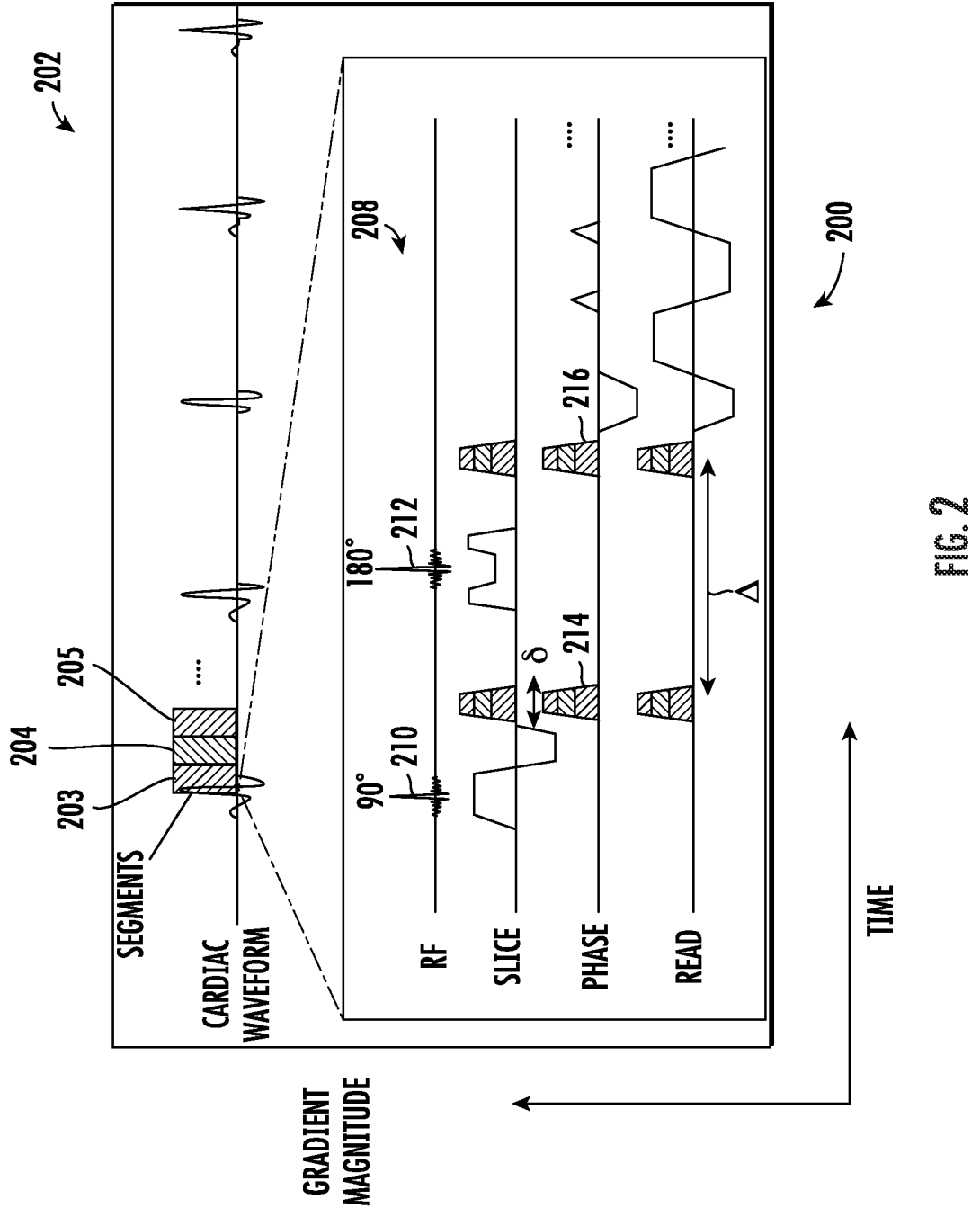
FIG. 2 illustrates a representative displacement encoding pulse sequence.

FIG. 2 illustrates a representative MRI pulse sequence 200 for E-tensor measurements based on a cardiac cycle that can be produced with the apparatus 100 of FIG. 1 or other MRI apparatus. Pulse sequences that can be used for measurement of a displacement field (i.e., displacements along multiple axes as a function of position in a specimen) are referred to herein as "displacement encodings." A cardiac waveform 202 is shown as divided into segments such as representative segments 203-205 during which displacement encoding pulse sequences are applied to measure tissue displacement ($u_1$, $u_2$, $u_3$) as a function of location, i.e., $u_1(x_1, x_2, x_3)$, etc. An RF pulse sequence 208 includes a 90 degree pulse 210 that rotates spins from a z-axis established with an axial magnetic field to an xy-plane and a 180 degree pulse 212 that inverts spin components. Displacement encoding is provided with a first encoding gradient pulse such as pulse 214 having an effective duration δ that is applied after the 90 degree pulse 210. A second encoding gradient pulse 216 is applied after an interval Δ (also referred to as a diffusion time) and after the 180 degree pulse. The gradient pulses 212, 214 are generally balanced so each has the same effective area (the product of pulse width and pulse amplitude). Such pulse sequences are applied on three independent directions for measurement of the displacement field; all can have the same effective area, but sequences for different directions can use different areas. A b-value for such sequences is $b=(\gamma G\delta)^2\Delta$ and a displacement weighting parameter is $\gamma G\delta\Delta$, wherein G is an effective amplitude of the gradient pulses. For large displacement weighting while keeping the b-value small, the squared term (i.e., the square of gradient pulse area) should be kept small while Δ should be large. This means applying gradients only for short times within the pulse interval Δ. This is contrary to conventional diffusion tensor imaging (DTI) approaches in which Δ is kept small to reduce echo times while the area under the gradient pulse is increased to achieve large b-values. Pulse intervals longer than 20 ms are generally unsuitable for DTI acquisitions.

In typical examples, displacement encoding pulse sequences are applied for cardiac cycle segments spanning a full cardiac cycle and all components of the displacement field $u_i$ are determined as functions of time in the cardiac cycle. FIG. 2 also shows readout and slice select pulse sequences used to acquire displacement-based signals responsive to displacement-encoding. Displacement-encoding gradient pulses are labeled only on the phase axis. Similar gradient pulses are shown on the slice and read axes but are not labeled. In general, such gradient pulses can be applied in any direction and multiple directions are needed to obtain a full E-tensor.

Displacement Encoding Using Ultrasound for E-Tensor Measurement

In typical examples, ultrasound imaging is used to generate and detect shear waves in 3D which are utilized to reconstruct the E-tensor. In some examples, the ultrasound excitation beam is steered to multiple orientations within the material with the resulting displacement measured in 3D for each orientation of the beam. This extends the number of governing equations of motion (Equation 2) beyond three which stabilize the fit further and improve the accuracy of the reconstructed E-tensor. In some examples, ultrasound is used to measure physiological displacements intrinsic to the organ under study to reconstruct the E-tensor.

To measure the 3D displacement field, a series of 3D ultrasound volume images of the material synchronized with the external stimulus or physiological signal are acquired over time using 2D array transducers at a high frame rate. The speckles in the individual ultrasound volumes are tracked in 3D using existing algorithms to measure the displacement field, $u_i$, at any given segment of the actuation cycle.

Cardiac Cycle Based System

Figure 3:
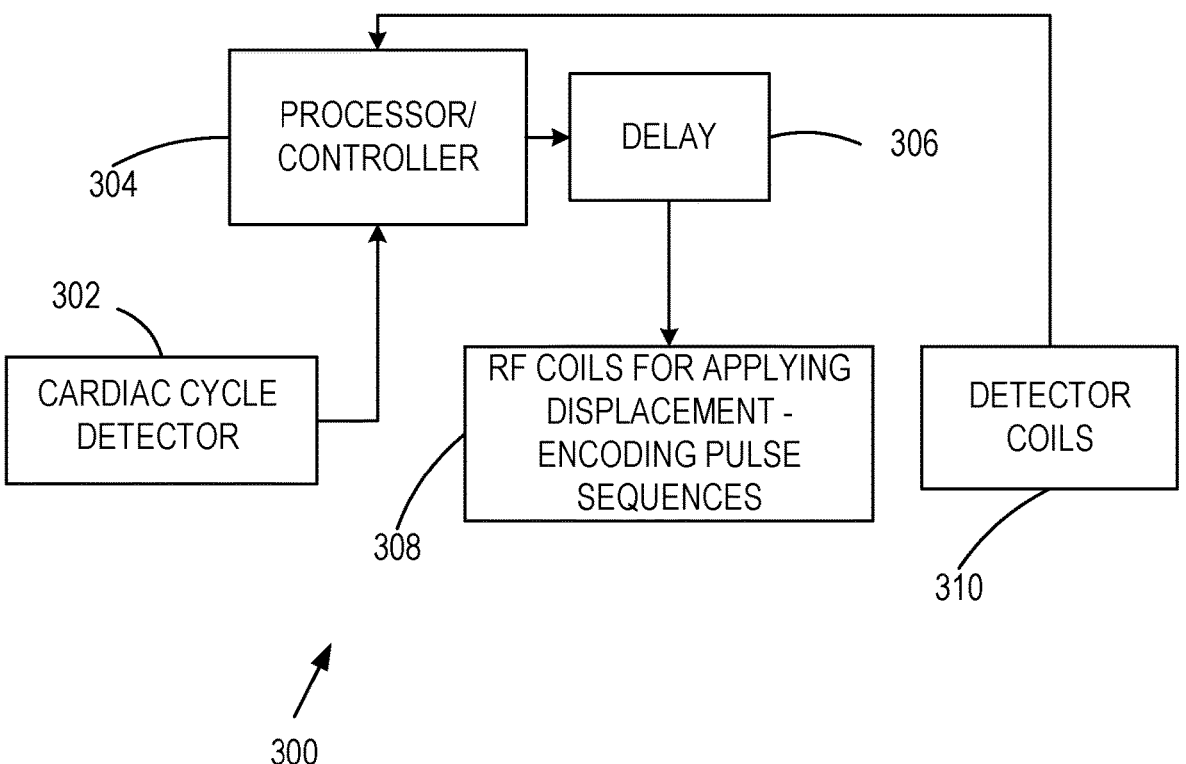
FIG. 3 illustrates a representative MR system configured to measure a displacement field of a specimen produced by cardiac pulsation.

Referring to FIG. 3, a representative MR system 300 includes a cardiac cycle detector 302 that is coupled to a subject to establish time references within cardiac cycles. A processor/controller 304 is coupled to the cardiac cycle detector 302 and initiates MR signal acquisition via a delay generator 306 that permits selection of a cardiac segment for displacement measurement. The delay generator 306 is shown as a separate component but suitable delays can be provided by the processor/controller 304 as well using, for example, a digital counter or other digital delay. One or more gradient coils 308 are energized to produce suitable displacement-encoding pulse sequences and subject response is detected with one or more detector coils 310 and a corresponding signal returned to the processor/controller 304. In some cases, the signal is returned as a digital signal but can also be returned as an analog signal that is digitized with an analog-to-digital converter (ADC) provided at or with the processor/controller 304. A series of delays can be provided by the delay generator 306 so that displacement ($u_1$, $u_2$, $u_3$) (i.e., the displacement field u as a function of time) is obtained for some or all voxels. The measured displacement field u can be processed in the MR system 300 to estimate the E-tensor if convenient, or can be directed to one or more additional processors for estimation and display of the E-tensor and other related quantities. Typically, a displacement field is measured at a single frequency as discussed below.

Elasticity Tensor Estimation

Methods and apparatus for measuring the specimen displacement field $u_i=(u_1, u_2, u_3)$ at one or more locations (such as voxels) in a specimen are described above. The measured displacement field permits estimation of the full E-tensor as discussed below. The governing equation for a displacement field for tissue or other materials within an MRI voxel consisting of an anisotropic, linearly-elastic material at the short time scales probed in elastography is given by the law of conservation of linear momentum, $$\rho \frac{\partial^2 u_i}{\partial t^2} = C_{islm} \frac{\partial^2 u_i}{\partial x_s \partial x_m} \tag{1}$$

where Einstein notation is used, $u_i \equiv u_i(x_i, t)$ is $i^{th}$-component of a measured time-dependent tissue displacement vector field, i, s, l, m are integer indices each ranging from 1 to 3, $\rho$ is tissue density, and $C_{islm}$ is a component of the full rank-4 E-tensor of interest, C. Assuming periodic excitation, a Fourier transform of the above equation in the time-domain results in the following system of partial differential equations, $$\omega_0^2 \rho \hat{u}_i(x_i, f_0) = -\frac{\partial^2 \hat{u}_i}{\partial x_s \partial x_m} C_{islm} = -H_{iam} C_{islm} = -A_{ij} c_j \tag{2}$$

where $\hat{u}_l$ is the complex displacement field as defined at an actuation frequency $f_0$, $\omega_0 = 2\pi f_0$, and $H_{lsm}$ is a rank-3 complex Hessian tensor with 18 independent components, $$H_{lsm} = \frac{\partial^2 \hat{u}_i}{\partial x_s \partial x_m}. \tag{3}$$

While a rank-3 tensor can have 27 independent elements, the Hessian tensor has only 18 independent elements as differentiation with respect to $x_s$ and $x_m$ produces the same value regardless of order.

Equation (2) above provides a means for determining the full E-tensor (i.e., C). The left-hand side requires the known angular frequency $\omega_0$, density $\rho$, and measured displacement field components $u_i$, filtered at the actuation frequency, i.e., $\hat{u}_i$. The right hand side includes derivatives of $\hat{u}_l$ based on the Hessian, $H_{lsm}$. The tensor contraction, $H_{lsm} C_{islm}$, in Equation 2 is expressed as the matrix-vector product, $A \vec{c}$, with the vector $\vec{c}$, comprising the unknown independent components of the E-tensor in the voxel, and A being a rectangular matrix of Hessian components as shown below for the general E-tensor with 21 independent components where $^T$ denotes transpose, $$A = \begin{bmatrix} H_{111} & 0 & 0 \\ H_{212} & H_{112} & 0 \\ H_{313} & 0 & H_{113} \\ H_{213}+H_{312} & H_{113} & H_{112} \\ 2H_{113}+H_{311} & 0 & H_{111} \\ 2H_{112}+H_{211} & H_{111} & 0 \\ 0 & H_{222} & 0 \\ 0 & H_{323} & H_{223} \\ 0 & 2H_{223}+H_{322} & H_{222} \\ H_{223} & H_{123}+H_{312} & H_{212} \\ H_{222} & H_{122}+2H_{212} & 0 \\ 0 & 0 & H_{333} \\ 0 & H_{333} & H_{233}+2H_{323} \\ H_{333} & 0 & H_{133}+2H_{313} \\ H_{323} & H_{313} & H_{123}+H_{213} \\ 0 & H_{233}+H_{323} & H_{223}+H_{322} \\ H_{233}+H_{323} & H_{133}+H_{313} & H_{123}+H_{213}+2H_{312} \\ H_{223}+H_{322} & H_{123}+2H_{213}+H_{312} & H_{212}+H_{212} \\ H_{133}+H_{313} & 0 & H_{113}+H_{311} \\ 2H_{123}+H_{213}+H_{312} & H_{113}+H_{311} & H_{112}+H_{211} \\ H_{122}+H_{212} & H_{112}+H_{211} & 0 \end{bmatrix}^T \quad \vec{c} = \begin{bmatrix} C_{1111} \\ C_{1122} \\ C_{1133} \\ C_{1123} \\ C_{1113} \\ C_{1112} \\ C_{2222} \\ C_{2233} \\ C_{2223} \\ C_{1322} \\ C_{1222} \\ C_{3333} \\ C_{2333} \\ C_{1333} \\ C_{1233} \\ C_{2323} \\ C_{1323} \\ C_{1223} \\ C_{1313} \\ C_{1213} \\ C_{1212} \end{bmatrix} \tag{4}$$

The unknown vector, $\vec{c}$, is estimated at each voxel by solving the following constrained optimization problem (i.e., finding the $c_j$ which minimizes the maximum residual among the three equations of motion such that the elasticity tensor is symmetric and positive definite), $$\min_{c_j} \max_{i \in \{1,2,3\}} \left| A_{ij} c_j + \omega_0^2 \rho \hat{u}_i \right| \tag{5}$$

$$\text{s.t. } C_{\theta \times \theta} \in \mathcal{M}_+ \tag{6}$$

where $C_{6 \times 6}$ is the E-tensor written in Voigt notation as a symmetric 6×6 matrix, and $M_+$ is a space of symmetric positive definite matrices. Additional explanation of the above can be reviewed in Helbig, G., "Foundations of anisotropy for exploration seismics," Handbook of Geophysical Exploration, Section I, Seismic Explorations, Vol. 22 (1994), which is herein incorporated by reference in its entirety. In Voigt notation, the rank-4 E-tensor with elements $C_{islm}$ is transformed into a symmetric square matrix $$\begin{bmatrix} C_{1111} & C_{1122} & C_{1133} & C_{1123} & C_{1131} & C_{1112} \\ C_{1122} & C_{2222} & C_{2233} & C_{2223} & C_{2231} & C_{2212} \\ C_{1133} & C_{2233} & C_{3333} & C_{3323} & C_{3331} & C_{3312} \\ C_{1123} & C_{2223} & C_{3323} & C_{2323} & C_{2331} & C_{2312} \\ C_{1131} & C_{2231} & C_{3331} & C_{2331} & C_{3131} & C_{3112} \\ C_{1112} & C_{2212} & C_{3312} & C_{2312} & C_{3112} & C_{1212} \end{bmatrix} \tag{7}$$

The positive definiteness constraint is imposed on the E-tensor to ensure mechanical stability of the material and numerical stability of the inversion algorithm. The data is fit to each of a number of E-tensor material models having different symmetries, (e.g., isotropic, cubic, triclinic, monoclinic, etc.) and the model likelihood is measured from the adjusted Akaike information criterion (AIC), used to select the model with greatest parsimony, which provides an optimal or other trade-off between goodness of fit and a number of free parameters as described in Burnham et al., "Model selection and inference: a practical information-theoretic approach," Springer (1998), which is incorporated by reference herein in its entirety. The noise amplification of the derivative operation is minimized by approximating the derivatives using local piece-wise quadratic polynomial interpolation as described in Lanczos, C., "Applied Analysis," Dover Publications (1988), which is incorporated by reference herein in its entirety. The form of rank-4 tensors for various symmetry groups is well known and can obtained from, for example, Nye, J., "Physical Properties of Crystals," Oxford, (1957), which is incorporated by reference herein in its entirety.

In typical examples, the Hessian is computed by fitting the measured displacement to a quadratic polynomial using 5 neighboring points for each direction using a least squares approach, assuming that the displacement is locally smooth in a 5 voxel×5 voxel×5 voxel cube. Fewer or more neighbors can be used. The volume size can be assigned a particular symmetry as discussed above so that large volumes (>5 voxel cubes) can result in averages of sample volumes containing structures of different symmetries. Smaller volumes can permit more accurate assessment of spatially varying symmetry changes.

Denoising the Displacement Field

Because determination of E-tensor elements is based on derivatives of the displacement field, it can be advantageous to reduce noise in the displacement field before taking spatial derivatives of its components that are used for computing the Hessian tensor. Smoothing of the displacement field is performed by imposing "compatibility conditions" that are constraints that ensure that the deformation field does not exhibit discontinuities (e.g., cracks, folds, or slips) in the material. They are given by the following relations in terms of the rank-4 St. Venant's tensor, $R_{ijkl}$ according to Georgiyevskii et al., "The number of independent compatibility equations in the mechanics of deformable solids," J. Applied Mathematics and Mechanics, 68(6):941-946 (2004), which is incorporated by reference herein in its entirety, $$R_{ijkl} = \frac{\partial^2 \epsilon_{ik}}{\partial x_j \partial x_l} + \frac{\partial^2 \epsilon_{jl}}{\partial x_i \partial x_k} - \frac{\partial^2 \epsilon_{il}}{\partial x_j \partial x_k} - \frac{\partial^2 \epsilon_{jk}}{\partial x_i \partial x_l} = 0 \tag{8}$$

where $\epsilon_{ij}$ is the rank-2 strain tensor obtained from the measured displacement field given by.

$$\epsilon_{ij} = \frac{1}{2}\left( \frac{\partial u_i}{\partial x_j} + \frac{\partial u_j}{\partial x_i} \right) \tag{9}$$

The displacement noise or perturbation field, being non-analytic, is not expected to obey the compatibility conditions. The displacement field can be denoised by solving the following constrained optimization problem locally (e.g., piecewise) for ease in computing while incorporating realistic discontinuities that may exist in composite materials, $$\min_{u_i^d} \left\| u_i^d - u_i \right\|^2 \tag{10}$$

$$\text{s.t. } \max_{j \in \{1,2,3,4,5,6\}} \left| R_j\left(u_i^d\right) \right| = 0 \tag{11}$$

where $u_i^d = u_i^d$ (x, y, z) is the denoised displacement field and $R_j$ is the vector consisting of six independent components of the St. Venant's tensor. The derivatives in the St. Venant's tensor can be approximated using the essentially non-oscillatory (ENO) numerical scheme to reduce numerical dissipation while maintaining accuracy, as described in Chi-Wang, "Essentially non-oscillatory and weighted essentially non-oscillatory schemes," Acta Numerica, 29:701-762 (2020), which is incorporated by reference herein in its entirety.

Microstructural Stains and Glyphs

Determination of the full E-tensor permits sophisticated analyses of specimens but the complex nature of the rank-4 E-tensor can be difficult to visualize or interpret. Measures derived from the full E-tensor can aid in appreciation of the E-tensor. The structure of the E-tensor can be visualized using a 3D glyph representing a characteristic quartic of the tensor, $r_i r_s r_i r_m C_{islm}$ (see, e.g., Helbig). The effective isotropic E-tensor of the medium is obtained by averaging the measured E-tensor uniformly over all possible orientations in a sphere, resulting in the following expression for the effective isotropic bulk modulus, K, and shear modulus, G, $$K = \frac{1}{9}Tr(D) \tag{12}$$

$$G = \frac{1}{30}(3Tr(V) - Tr(D)) \tag{13}$$

where Tr(A) refers to trace of a matrix, A, and $D=C_{isll}$, $V=C_{isls}$ are the rank-2 dilatational and Voigt stiffness tensors, respectively as discussed in Helbig. A scalar invariant mechanical anisotropy stain, MA, is defined as the Riemannian distance between the measured E-tensor and an effective isotropic E-tensor, which lies in the manifold of positive definite matrices as shown below:

$$MA = \sqrt{\sum_{i=1}^{6} \log^2\left[\lambda_i\left(C_{6\times6}^{-1} C_{6\times6}^{iso}\right)\right]} \tag{14}$$

where $\lambda_i(A)$ is the $i^{th}$ eigenvalue of the matrix, A, and $C_{6\times6}^{iso}$ is the effective isotropic E-tensor expressed in Voigt notation as a symmetric 6×6 matrix. The proposed scalar anisotropy measure is also dimensionless or unitless and takes a value of zero if the measured E-tensor is isotropic and increases with increasing anisotropy of the E-tensor. An invariant measure of bulk average stiffness, AS, is obtained by taking the average trace of the effective isotropic E-tensor as shown below, $$AS = \frac{1}{6}Tr\left(C_{6\times6}^{iso}\right) \tag{15}$$

All the above stains (i.e., K, G, MA and AS) and the E-tensor quartic glyph can be measured and mapped for the whole brain (or generally the entire imaging volume) to visualize and help analyze the distribution and spatial variation of mechanical properties. These may serve as quantitative radiological imaging biomarkers for disease, development, aging, and trauma.

Representative Methods

Figure 4A:
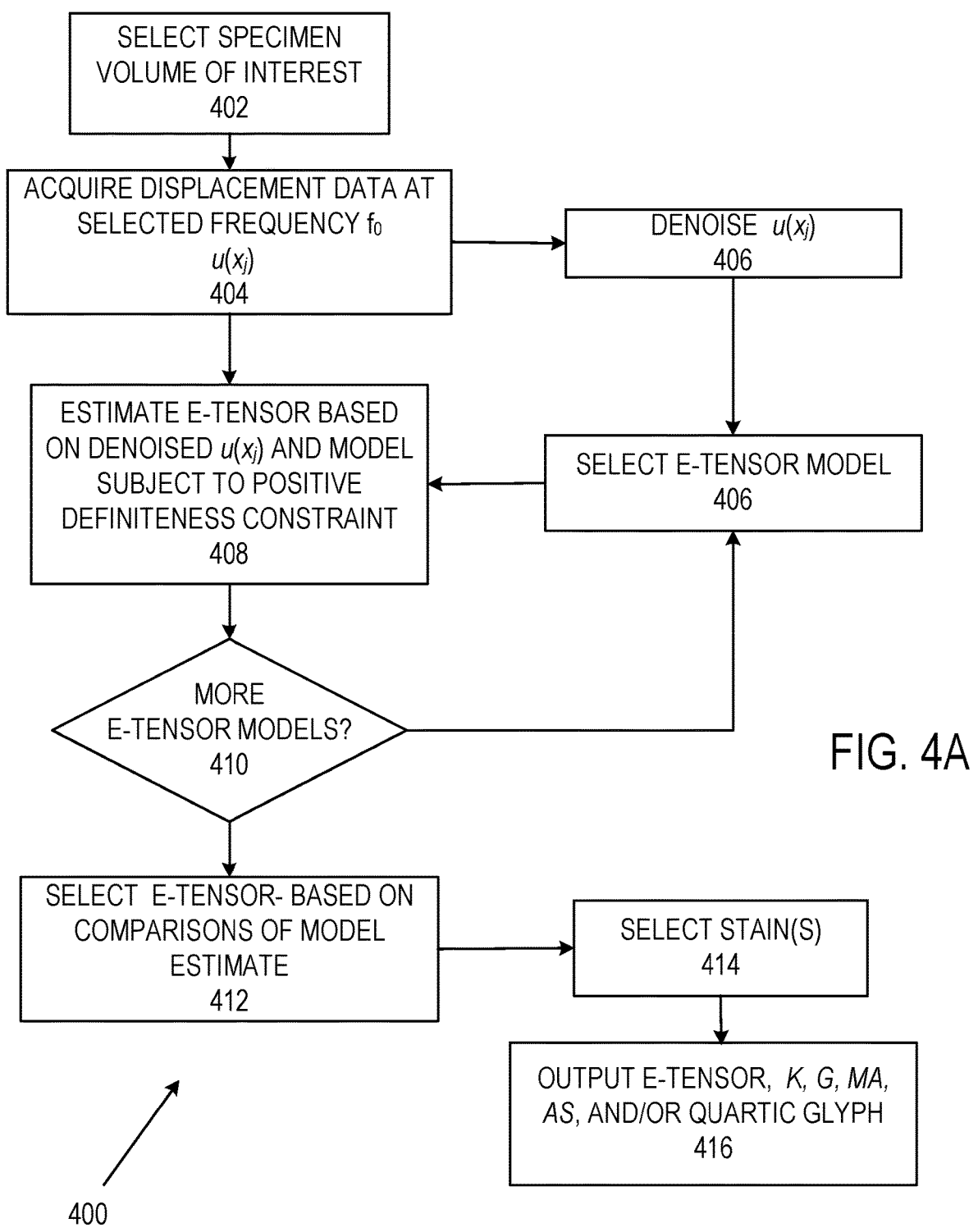
FIG. 4 illustrates a representative method of obtaining estimates of a full elasticity tensor (E-tensor).

Referring to FIG. 4A, a representative method 400 includes selecting a volume of interest at 402 and acquiring displacement data (i.e., the displacement field û for an excitation frequency $f_0$ at 404). At 406, the displacement field is denoised as discussed above. At 407, a tensor symmetry model is selected and at 408, the E-tensor is estimated based on the selected model. If additional tensor models are to be evaluated as indicated at 410, an additional model is selected and the E-tensor estimated based on the additional model. With all tensor models of interest used to produce respective E-tensor estimates, the estimates are compared and a particular model is selected at 412 based on, for example, a trade-off between goodness of fit and a number of elements as discussed above. One or more stains such as K, G, MA, AS, and the E-tensor quartic glyph can be selected at 414 and computed at 416.

Figure 4B:
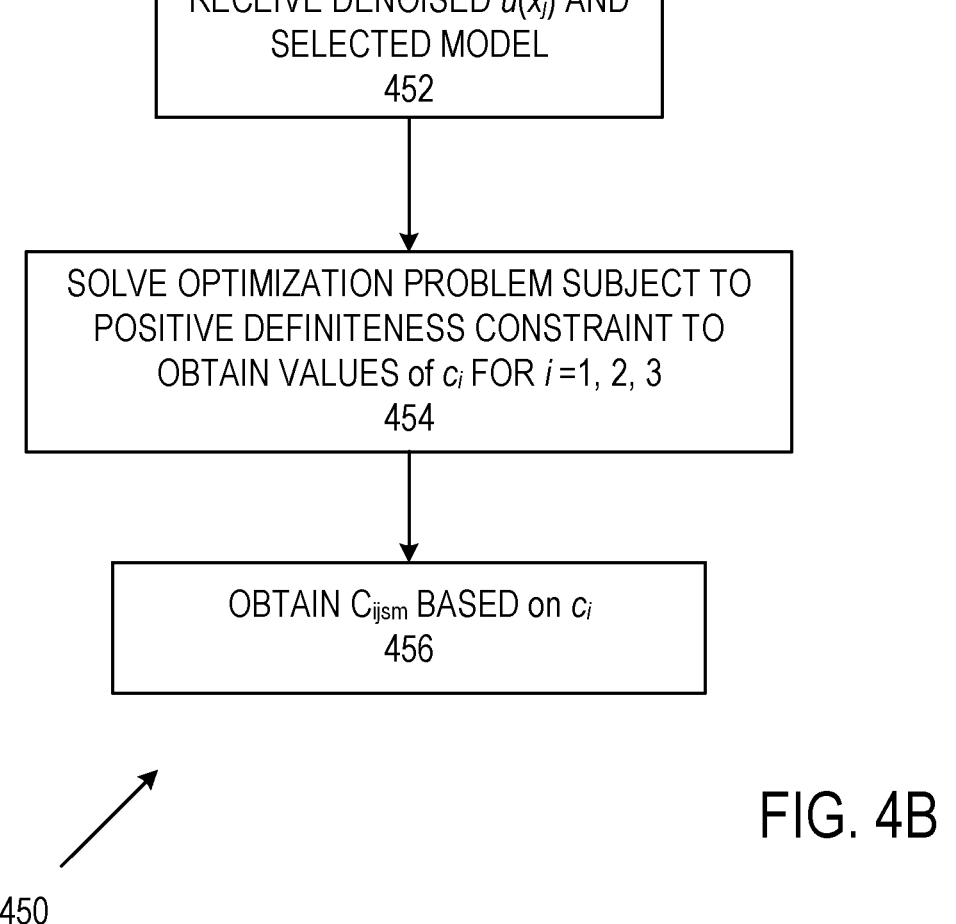

Referring to FIG. 4B, a representative method 450 of determining an E-tensor estimate based on the measured displacement field includes receiving the denoised displacement field and a selected E-tensor model at 452. At 454 an optimization problem is solved subject to a positive definiteness constraint to obtain values for the components of $\vec{c}$. At 456, these values are used to determine values of the E-tensor elements $C_{ilsm}$.

Simulation

The efficacy of the proposed methods in reconstructing the E-tensor is tested using synthetic 4D displacement vector fields generated from well-known wave-type solutions to the governing equations. The displacement in a numerical phantom with a known E-tensor distribution (isotropic on the left half-space and anisotropic on the right half-space to represent gray and white matter respectively) due to an incident wave is calculated analytically and used to reconstruct the E-tensor map of the phantom with the proposed method. Gaussian noise was added to the displacement field to evaluate the robustness of the reconstruction pipeline to noise.

A 2-parameter isotropic and a 9-parameter orthotropic E-tensor reported in literature for human brain gray and white matter in vivo at 50 Hz was used in the numerical phantom. The simulation was performed using the following parameters: $\rho=1000$ kg/m$^3$, field of view=24 cm×24 cm×3 cm with a matrix size equal to 80×80×10, incident wave direction $$= \left(0, \frac{1}{\sqrt{2}}, \frac{1}{\sqrt{2}}\right)$$

actuation frequency=50 Hz, and the frequency at which the displacement is sampled=250 Hz. The noise standard deviation was chosen such that the maximum displacement-noise-ratio (DNR) was 5 to simulate the worst-case scenario.

Figure 5:
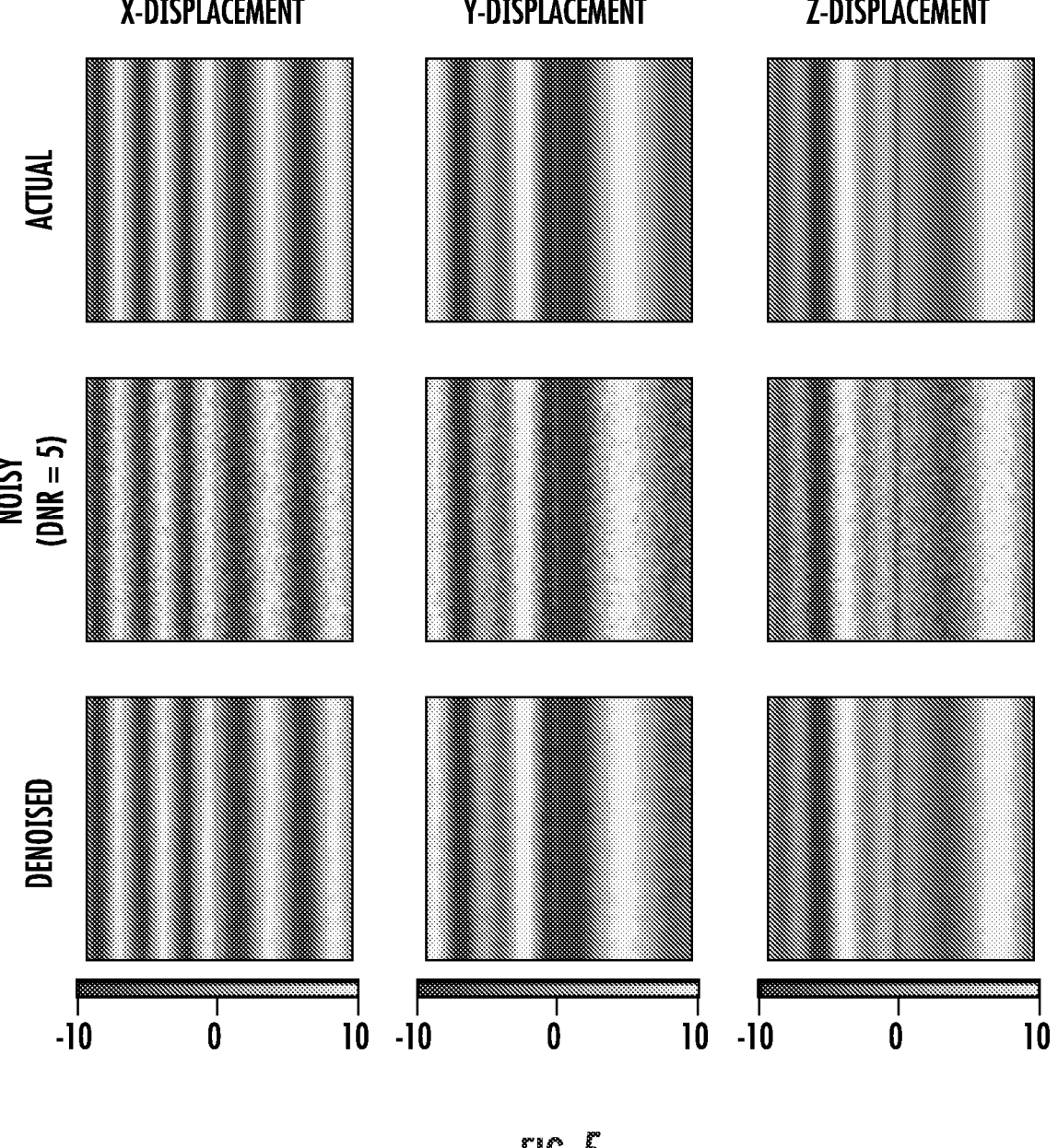
FIG. 5 shows actual, noisy and denoised x, y, and z components of a real part of a simulated displacement field at an actuation frequency in a center slice of a numerical phantom.
Figure 6:
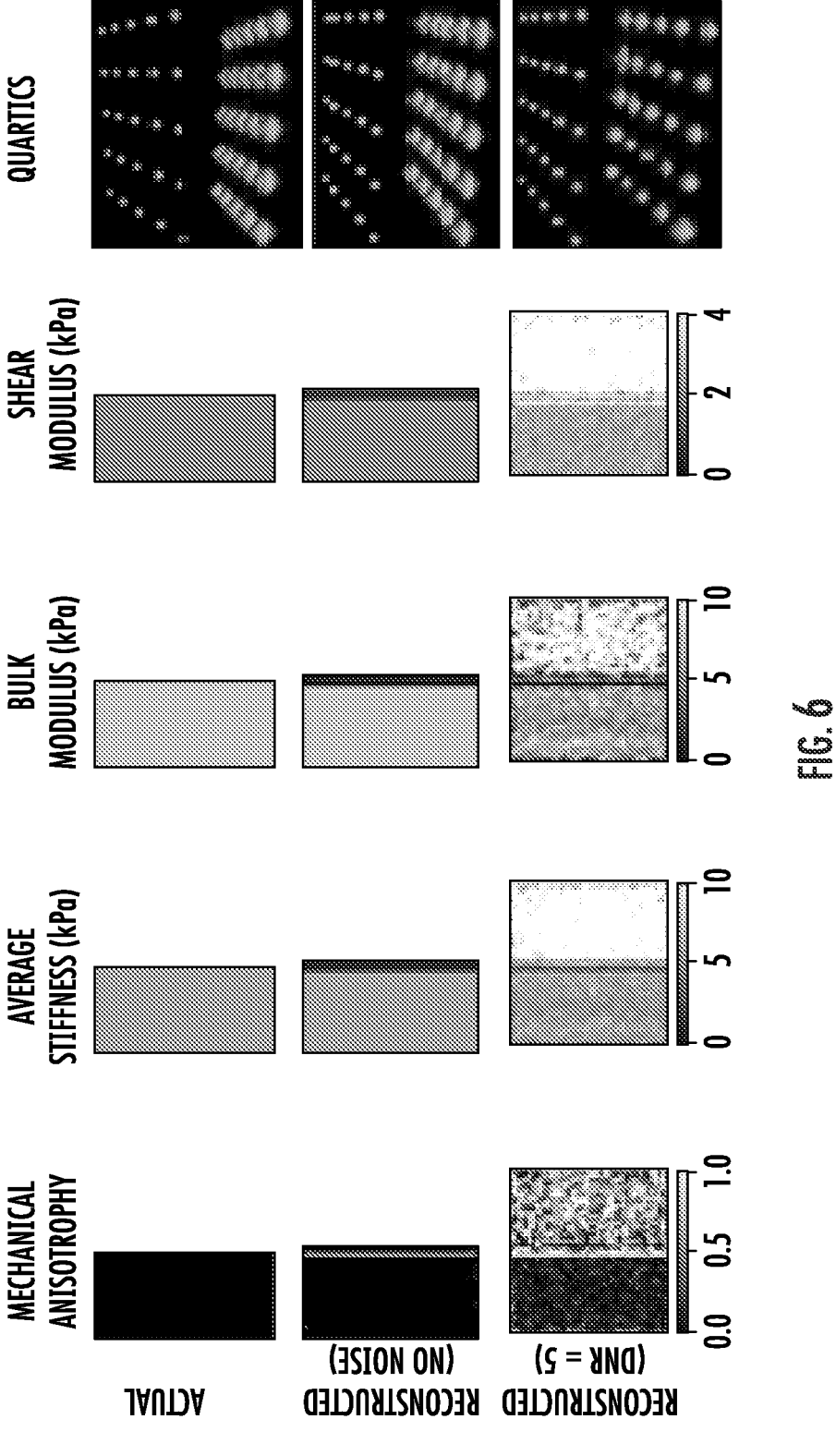
FIG. 6 shows maps of the mechanical anisotropy, average stiffness, isotropic bulk, and shear modulus stains along with quartic glyphs in a region of interest (ROI) in left (shown on top) and right (shown on bottom) half spaces of the numerical phantom. The maps and glyphs are shown for the actual and reconstructed E-tensors with and without noise in the displacement field.

The simulated displacement maps in FIG. 5 exhibit the efficacy of the denoising strategy. Quantitative noise analysis of the displacement maps showed that the DNR approximately doubled with denoising. The stains and glyphs for actual and reconstructed E-tensors in the simulation are shown in FIG. 6. It can be observed that the mechanical anisotropy stain is zero for the isotropic E-tensor and close to one for the anisotropic E-tensor, which is consistent with ground-truth. The stains and glyphs for the reconstructed phantom also match well with the actual phantom in the presence and absence of noise except at the boundaries where the material properties can change abruptly.

Phantom MRI Measurements

The E-tensor reconstruction method can be tested in a phantom using an external tamper. A piston driven by a motor capable of operating from 1-20 Hz is mechanically coupled to the inside of a 50 mL tube containing 0.16% agarose gel. The adhesion of the gel to the walls of the tube generates radial shear waves within the gel which is used to measure its E-tensor. A piece of mushroom stalk soaked in water can be embedded in the gel to introduce anisotropy along with 0.01% sodium azide to prevent bacterial degradation.

MRI data can be acquired using a 30 mm quadrature radiofrequency (RF) probe (e.g., MicWB40, Bruker Biospin, Billerica, MA) on a 7T vertical Bruker wide-bore Avance III MRI scanner (e.g., Bruker Biospin, Billerica, MA) equipped with a Micro2.5 microimaging probe and three GREAT60 gradient amplifiers. The actuation cycle is evenly divided into 5-10 segments and the displacement field at each segment is measured using the MRI pulse sequence shown in FIG. 2 synchronized to the actuation cycle. The displacement field is obtained by solving the linear system of equations which relate the image phase with displacement encoding q-vectors.

Single-shot echo-planar imaging (EPI) acquisition can be performed using the following parameters: $\delta/\Delta=2/5$ ms, TR/TE=500/9 ms and 1 average with 500 μm isotropic spatial resolution. A total of 4 displacement encoded images can be obtained per segment with q-vectors oriented along the edges of a tetrahedron (i.e., Hadamard encoding) with the velocity encoding value, $u_{enc}$, equal to 2.5 mm/s. The phase images were unwrapped in q-space prior to displacement estimation. The measurement can be repeated with different shear wave frequencies to obtain the dispersion of E-tensor. A DTI acquisition with same field of view and resolution can be acquired with b=0, 1000 s/mm² to compare the diffusion tensor with E-tensor.

Tamperless Brain MR Tensor Elastography

The above methods can be applied to tamperless brain MR tensor elastography. The brain tissue displacement due to incoming blood flow from the heart is measured using cardiac-gated phase contrast MRI with spin-echo echo-planar imaging (EPI) MRI sequence shown in FIG. 2. The displacement encoding gradients (DEG) in the pulse sequence are placed farther apart to increase the sensitivity for small coherent displacements which result from cardiac pulsation while reducing diffusion weighting. The MRI data is acquired continuously over multiple heart beats and retrospectively binned into discrete segments of the cardiac cycle using simultaneously recorded cardiac waveforms. The 3D displacement vector field at each cardiac segment is obtained by solving the linear system of equations which relate the MRI phase and tissue displacement along the given DEG direction. The orientations of DEGs were uniformly distributed in a hemisphere to reduce the condition number of the encoding matrix used to invert the MRI phase at each cardiac segment. The phase errors resulting from DEG dependent artifacts such as due to eddy currents and bulk head motion can be removed by fitting the MRI phase measured in the scalp in each slice to a linear polynomial whose coefficients were used to correct the phase inside the brain.

MRI measurements can be performed using Siemens 3T Prisma clinical scanner equipped with a maximum gradient strength of 80 mT/m per axis and a 20-channel radiofrequency (RF) coil. Whole brain MRE scans along 128 DEG directions can be acquired using the aforementioned multi-slice EPI sequence with the following parameters: TR/TE=4800/77 ms, matrix size=70×70×50, field of view: 210 mm×210 mm×150 mm, and $\delta/\Delta=7/48$ ms resulting in a velocity encoding factor, $u_{enc}$ approximately equal to 700 μm/s or an equivalent displacement encoding of 34 μm which is a factor of two smaller than typical DENSE measurements. Diffusion tensor imaging (DTI) scans can be performed using the same field of view and spatial resolution with diffusion weighting factor, b=0, 1000 s/mm² to compare the measured E-tensor with the diffusion tensor.

Additional Examples and Applications

While acquisition of the displacement field can be based on MRI or ultrasound techniques, other approaches can provide displacement field values for processing as described above. The cardiac cycle is convenient as an excitation source for displacement field measurement, but other physiological motion such as respiration can be used as well as tamper-based excitation. For such measurements, gating of data acquisition is not required and measurements can be associated with cardiac or respiration cycle timing after acquisition. Because the approaches can use the Hessian operator, E-tensor results tend to be insensitive to bulk motion of a subject or specimen. Tamperless measurements of remote subjects are possible, for example, measurements of placental or fetal E-tensor values. The dependence of E-tensor values on frequency (dispersion) can also be determined using multi-frequency excitation or based on frequency components of a single frequency periodic excitation that can nevertheless have multiple frequency components. For example, a tamper-based excitation can be applied at a fixed frequency but will generally have a spectrum that includes components at multiple frequencies.

Computation and Control Systems

Figure 7:
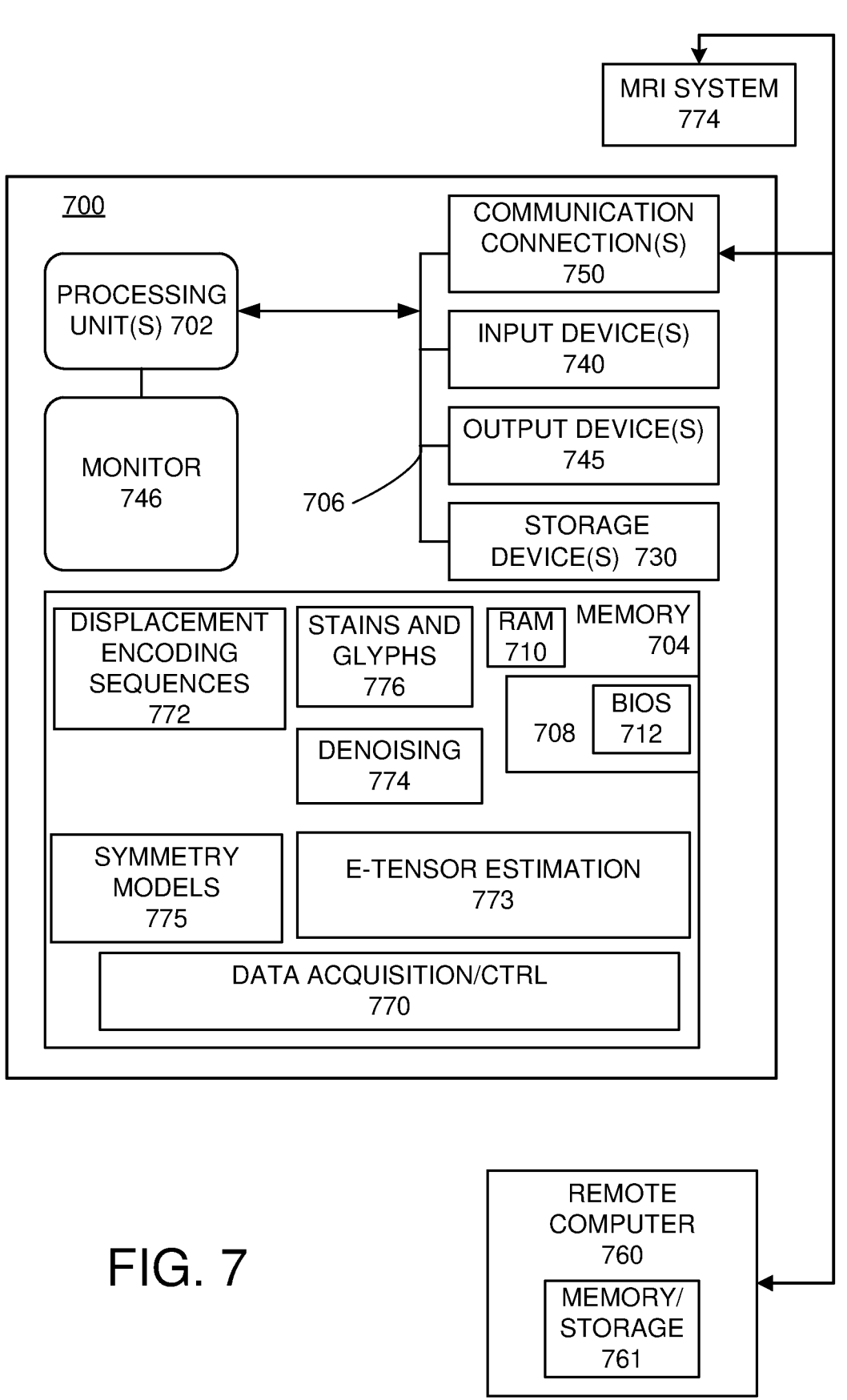
FIG. 7 illustrates a representative computing environment for performing any of the disclosed methods.

FIG. 7 and the following discussion are intended to provide a brief, general description of an exemplary computing/data acquisition environment in which the disclosed technology may be implemented. Although not required, the disclosed technology is described in the general context of computer executable instructions, such as program modules, being executed by a personal computer (PC), a mobile computing device, tablet computer, or other computational and/or control device. Generally, program modules include routines, programs, objects, components, data structures, etc., that perform particular tasks or implement particular abstract data types. Moreover, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 7, an exemplary system for implementing the disclosed technology includes a general purpose computing device in the form of an exemplary conventional PC 700, including one or more processing units 702, a system memory 704, and a system bus 706 that couples various system components including the system memory 704 to the one or more processing units 702. The system bus 706 may be any of several types of bus structures including a memory bus or memory controller, a peripheral bus, and a local bus using any of a variety of bus architectures. The exemplary system memory 704 includes read only memory (ROM) 708 and random access memory (RAM) 710. A basic input/output system (BIOS) 712, containing the basic routines that help with the transfer of information between elements within the PC 700, is stored in ROM 708. The exemplary PC 700 further includes one or more storage devices 730 such as a hard disk drive for reading from and writing to a hard disk, a magnetic disk drive for reading from or writing to a removable magnetic disk, an optical disk drive for reading from or writing to a removable optical disk (such as a CD-ROM or other optical media), and a solid state drive. Such storage devices can be connected to the system bus 706 by a hard disk drive interface, a magnetic disk drive interface, an optical drive interface, or a solid state drive interface, respectively. The drives and their associated computer readable media provide nonvolatile storage of computer-readable instructions, data structures, program modules, and other data for the PC 700. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices 730 or the memory 704 including an operating system, one or more application programs, other program modules, and program data. A user may enter commands and information into the PC 700 through one or more input devices 740 such as a keyboard and a pointing device such as a mouse. Other input devices may include a digital camera, microphone, joystick, game pad, satellite dish, scanner, or the like. These and other input devices are often connected to the one or more processing units 702 through a serial port interface that is coupled to the system bus 706, but may be connected by other interfaces such as a parallel port, game port, or universal serial bus (USB). A monitor 746 or other type of display device is also connected to the system bus 706 via an interface, such as a video adapter. Other peripheral output devices, such as speakers and printers (not shown), may be included.

The PC 700 may operate in a networked environment using logical connections to one or more remote computers, such as a remote computer 760. In some examples, one or more network or communication connections 750 are included. The remote computer 760 may be another PC, a server, a router, a network PC, or a peer device or other common network node, and typically includes many or all of the elements described above relative to the PC 700, although only a memory storage device 761 has been illustrated in FIG. 7. The personal computer 700 and/or the remote computer 760 can be connected to a logical a local area network (LAN) and a wide area network (WAN). Such networking environments are commonplace in offices, enterprise wide computer networks, intranets, and the Internet.

When used in a LAN networking environment, the PC 700 is connected to the LAN through a network interface. When used in a WAN networking environment, the PC 700 typically includes a modem or other means for establishing communications over the WAN, such as the Internet. In a networked environment, program modules depicted relative to the personal computer 700, or portions thereof, may be stored in the remote memory storage device or other locations on the LAN or WAN. The network connections shown are exemplary, and other means of establishing a communications link between the computers may be used.

The memory 704 generally includes computer-executable instructions for selecting displacement encoding sequences, E-tensor estimation, denoising of displacement fields, selection and characterization of symmetry models, and stain and glyph computation at respective memory portions 772-776. Computer-executable instructions for data acquisition and instrument control can be stored in a memory portions 770. Acquired and processed data (e.g., images based on mean diffusion tensor images) can be displayed using computer-executable instructions stored in the memory 704 as well. As noted above, data acquisition, processing, and instrument control can be provided at an MRI system or distributed at one or more processing devices using a LAN or WAN.

General Considerations

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items. The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation. Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus are referred to as "lowest," "best," "minimum," or the like. It will be appreciated that such descriptions are intended to indicate that a selection among many used functional alternatives can be made, and such selections need not be better, smaller, or otherwise preferable to other selections. Examples are described with reference to directions indicated as "above," "below," "upper," "lower," and the like. These terms are used for convenient description, but do not imply any particular spatial orientation.

The term "image" is used herein to refer to displayed image such as on a computer monitor, or digital or analog representations that can be used to produce displayed images. Digital representations can be stored in a variety of formats such as JPEG, TIFF, or other formats. Image signals can be produced using an array detector or a single element detector along with suitable scanning of a sample.

In view of the many possible embodiments to which the principles of the disclosure may be applied, it should be recognized that the illustrated embodiments are only preferred examples and should not be taken as limiting the scope of the disclosure.

The invention claimed is:

1. A method, comprising:

obtaining, using a magnetic resonance (MR) apparatus, a displacement field within a specimen, wherein the MR apparatus comprises a magnet operable to establish an axial magnetic field, at least gradient coil situated to apply displacement-sensitizing gradient pulses to the specimen situated in the axial magnetic field, at least one receiver coil situated to receive MR signals responsive to the displacement-sensitizing gradient pulses, and a processor, wherein the MR signals indicate the displacement field within the specimen; and estimating at least two elements of an elasticity tensor associated with at least one voxel of the specimen based on the displacement field, a select frequency the associated with the displacement field, and a tissue density of th specimen.

2. The method of claim 1,
wherein the displacement field is obtained based on a plurality of multidirectional displacement-sensitized magnetic resonance signals associated with the specimen at the selected frequency.

3. The method of claim 2, wherein the multidirectional displacement-sensitized magnetic resonance signals are associated with a plurality of voxels, the displacements of the displacement field are determined for each of the plurality of voxels, and the at least two elements of the elasticity tensor associated with the specimen are determined for each of the plurality of voxels.

4. The method of claim 3, wherein the estimate of the at least two elements of the elasticity tensor is determined with the at least two elements constrained to be positive definite.

5. The method of claim 1, wherein the estimate of the at least two elements of the elasticity tensor is determined based on symmetry group compatibility.

6. The method of claim 1, wherein the at least two elements of the elasticity tensor includes all elements of the elasticity tensor.

7. The method of claim 1, further comprising denoising the displacement field and estimating the at least two elements of the elasticity tensor based on the denoised displacement field.

8. The method of claim 1, wherein the displacement field is denoised using compatibility conditions.

9. The method of claim 2, further comprising obtaining the multidirectional displacement-sensitized magnetic resonance signals by applying, using the magnetic resonance (MR) apparatus, the displacement-sensitizing gradient pulses, wherein the displacement-sensitizing gradient pulses comprise a plurality of gradient pulse pairs with a temporal separation of at least 20 millisecond (ms) and a 180 degree pulse between each of the gradient pulse pairs.

10. The method of claim 2, further comprising obtaining the multidirectional displacement-sensitized magnetic resonance signals by applying, using the magnetic resonance (MR) apparatus, the displacement-sensitizing gradient pulses, wherein the displacement-sensitizing gradient pulses comprise a plurality of displacement-sensitizing gradient pulse pairs, each pulse of the pulse pair having a b-value of less than 500 s/mm$^2$, wherein b=$\gamma^2$G$^2\delta^2$($\Delta$–$\delta$/3), and wherein $\gamma$ is a gyromagnetic ratio, G is an effective gradient amplitude, $\delta$ is effective pulse width, and $\Delta$ is pulse separation.

11. The method of claim 1, further comprising processing the estimate of the at least two elements of the elasticity tensor to produce an orientation invariant indicator of specimen elasticity, and
wherein the orientation invariant indicator of specimen elasticity is one or more of a bulk average stiffness, a mechanical anisotropy, a bulk shear modulus, or an effective anisotropy.

12. The method of claim 1, further comprising processing the estimate of the at least two elements of the elasticity tensor to produce a visual indicator of specimen elasticity, wherein the visual indicator is a glyph.

13. The method of claim 2, further comprising obtaining the multidirectional displacement-sensitized magnetic resonance signals by applying, using a magnetic resonance (MR) apparatus, the displacement-sensitizing gradient pulses, wherein displacement-sensitizing gradient pulses comprise gradient pulse pairs at a plurality of times within a specimen excitation period.

14. The method of claim 2, further comprising applying a mechanical disturbance at the selected frequency with an actuator, wherein the plurality of multidirectional displacement-sensitized magnetic resonance signals associated with the specimen are responsive to the applied mechanical disturbance.

15. A magnetic resonance (MR) apparatus, comprising:
a magnet operable to establish an axial magnetic field;
at least one gradient coil situated to apply displacement-sensitizing gradient pulses to a specimen situated in the axial magnetic field;
at least one receiver coil situated to receive MR signals responsive to the displacement-sensitizing gradient pulses, wherein the MR signals indicate a displacement field within the specimen; and
a processor configured to receive the MR signals and produce an estimate of at least two components of an elasticity tensor associated with at least one voxel of the specimen based on the displacement field, a selected frequency that is associated with the displacement field, and a tissue density of the specimen.

16. The MR apparatus of claim 15, wherein the processor is configured to produce an estimate of all components of the elasticity tensor for a plurality of voxels, and wherein the processor is configured to produce at least one orientation invariant index of elasticity based on the components of the elasticity tensor for the plurality of voxels.

17. The MR apparatus of claim 15, wherein the at least one gradient coil is operable to produce gradient pulse pairs about a 180 degree RF pulse and having a temporal separation of at least 20 milliseconds (ms).

18. The MR apparatus of claim 15, wherein the processor is configured to determine the displacement field based on the MR signals, denoise the displacement field, and produce a full elasticity tensor based on the denoised displacement field, and
wherein the denoising of the displacement field is based on compatibility conditions.

19. The MR apparatus of claim 15, wherein the processor is configured to estimate all components of the elasticity tensor based on at least one of:
a positive definiteness constraint; or
a comparison of elasticity tensors calculated based on two or more symmetry conditions.

20. The MR apparatus of claim 15, wherein the displacement-sensitizing gradient pulses comprise gradient pulse pairs at a plurality of times within a specimen excitation period, wherein a specimen excitation within the specimen excitation period is produced in vivo by one or more heartbeats.

\* \* \* \* \*